US00PP37215P2

(12) United States Plant Patent
van Swieten

(10) Patent No.: US PP37,215 P2
(45) Date of Patent: Jan. 13, 2026

(54) ***PHALAENOPSIS* PLANT NAMED 'PHA964388'**

(50) Latin Name: *Phalaenopsis hybrida*
Varietal Denomination: PHA964388

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/770,002

(22) Filed: Jul. 11, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'PHA964388', characterized by its upright plant habit; upright flowering stems; freely flowering habit with typically two inflorescences developing per plant, each inflorescence with numerous flowers; light purple-colored flowers with purplish red-colored spots and blotches and yellow and white-colored labella.

2 Drawing Sheets

Figure 1:
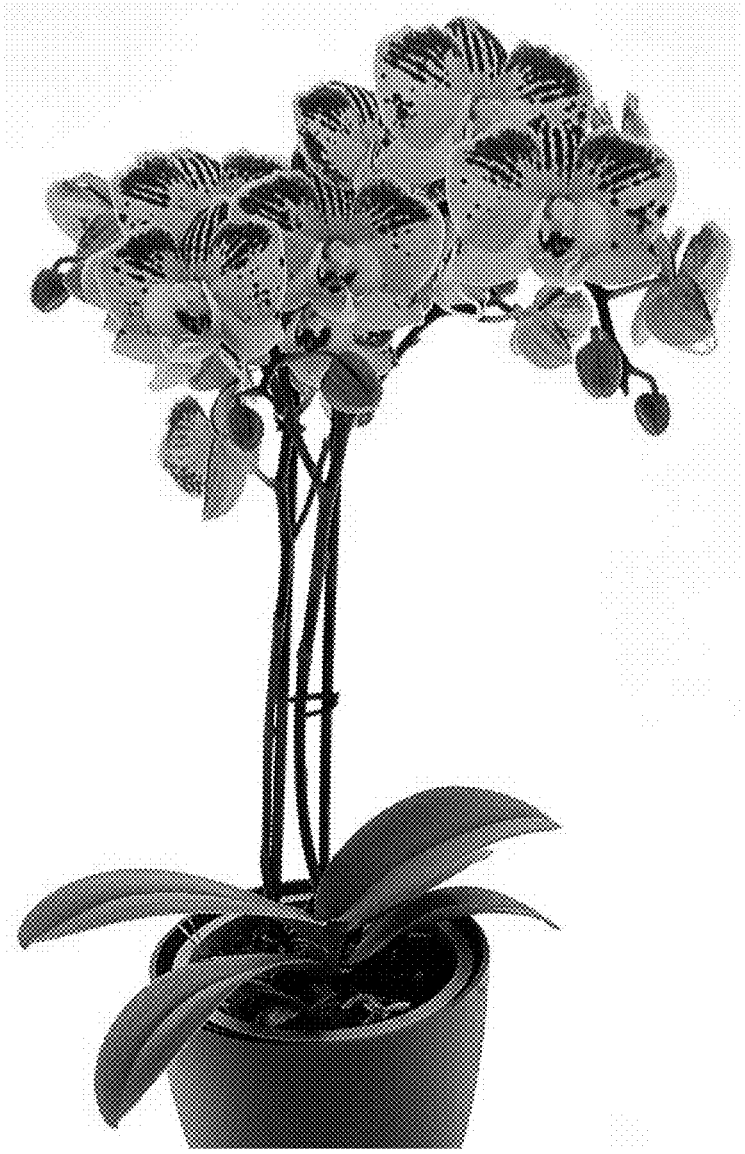

Botanical designation: *Phalaenopsis hybrida.*
Cultivar denomination: 'PHA964388'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Apr. 19, 2023, application number 2023/0885. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida,* and hereinafter referred to by the name 'PHA964388'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique patterns and coloration.

The new *Phalaenopsis* plant originated from a cross-pollination in February 2017 in Bleiswijk, The Netherlands of a proprietary selection of *Phalaenopsis hybrida* identified as code number 10-43698-02, not patented, as the female, or seed, parent with a proprietary selection of *Phalaenopsis hybrida* identified as code number 13-55325-02, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in October 2019.

Asexual reproduction of the new *Phalaenopsis* plant by in vitro meristem propagation in a controlled environment in Bleiswijk, The Netherlands since October 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA964388'. These characteristics in combination distinguish 'PHA964388' as a new and distinct *Phalaenopsis* plant:

1. Upright plant habit.
2. Upright flowering stems.
3. Freely flowering habit with typically two inflorescences developing per plant, each inflorescence with numerous flowers.
4. Light purple-colored flowers with purplish red-colored spots and blotches and yellow and white-colored labella.

Plants of the new *Phalaenopsis* can be compared to plants of the female parent selection. Plants of the new *Phalaen-*

*opsis* differ primarily from plants of the female parent selection in flower size as flowers of plants of the new *Phalaenopsis* are narrower than and not as broad as flowers of plants of the female parent selection. In addition, petals of plants of the new *Phalaenopsis* do not have any netting patterns whereas petals of plants of the female parent selection have moderate to dense netting patterns.

Plants of the new *Phalaenopsis* can be compared to plants of the male parent selection. Plants of the new *Phalaenopsis* differ primarily from plants of the male parent selection in flower color as the central lobe of the labella of plants of the new *Phalaenopsis* are yellow and white in color whereas the central lobe of the labella of petals of plants of the male parent selection are reddish purple in color. In addition, the cirrhose tips of the labella of plants of the new *Phalaenopsis* are longer than the cirrhose tips of the labella of plants of the male parent selection.

Plants of the new *Phalaenopsis* can be compared to plants of *Phalaenopsis hybrida* 'PHALGETWO', disclosed in U.S. Plant Pat. No. 32,956. In side-by-side comparisons, plants of the new *Phalaenopsis* differ primarily from plants of 'PHALGETWO' in the following characteristics:

1. Flowers of plants of the new *Phalaenopsis* are narrower than and not as broad as flowers of plants of 'PHALGETWO'.
2. Petal apices of plants of the new *Phalaenopsis* are obtuse whereas petal apices of plants of 'PHALGETWO' are emarginate.
3. The central lobe of the labella of plants of the new *Phalaenopsis* are yellow and white in color whereas the central lobe of the labella of plants of 'PHALGETWO' are purplish red in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA964388' grown in a container.

Figure 2:
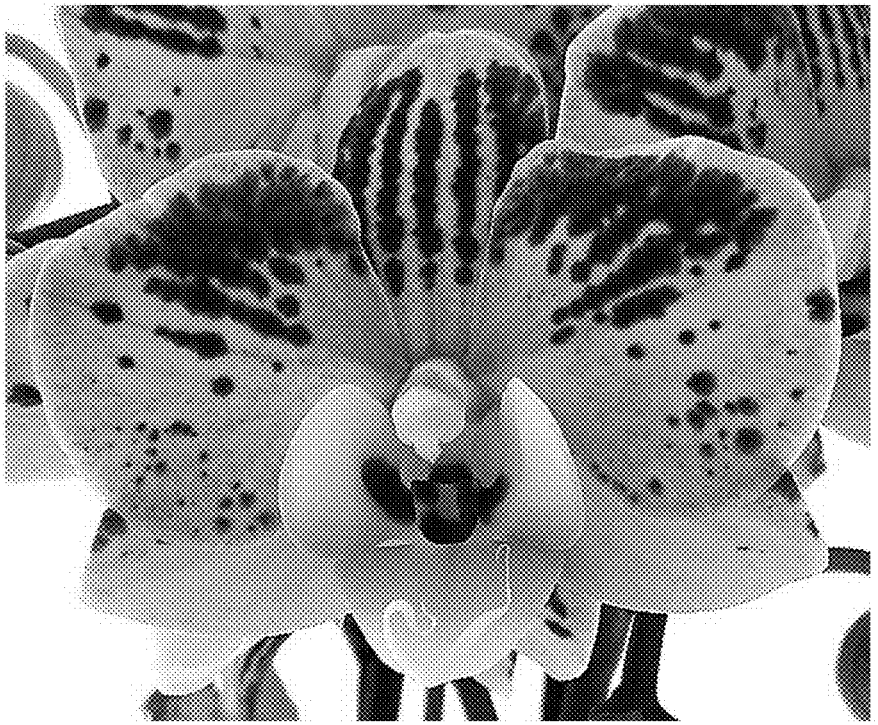

The photograph on the second sheet (FIG. 2) is a close-up view of a typical flower of 'PHA964388'.

DETAILED BOTANICAL DESCRIPTION

The aforementioned photographs and following observations and measurements describe plants grown during the early autumn in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA964388'.

Parentage:

*Female, or seed, parent*.—Proprietary selection of *Phalaenopsis hybrida* identified as code number 10-43698-02, not patented.

*Male, or pollen, parent*.—Proprietary selection of *Phalaenopsis hybrida* identified as code number 13-55325-02, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial.

*Plant height, substrate level to top of foliar plane*.—About 6.9 cm.

*Plant height, substrate level to top of floral plane*.—About 31.5 cm.

*Plant diameter or spread*.—About 21.6 cm.

Leaf description:

*Arrangement and quantity*.—Distichous, simple; sessile; about four to six fully-developed leaves per plant.

*Length*.—About 12.4 cm.

*Width*.—About 5.4 cm.

*Aspect*.—Semi-erect to horizontal.

*Shape*.—Narrowly oblong to oblanceolate; slightly to moderately carinate and slightly curled downward.

*Apex*.—Broadly and unequal obtuse.

*Base*.—Sheathing. Sheath length: About 1.4 cm. Sheath width: About 1 cm. Sheath color: Close to a blend of 144A and 144B; towards the margins, close to 144A.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B; at the margins, close to 137B. Developing leaves, lower surface: Close to 147B; at the margins, close to 145A. Fully expanded leaves, upper surface: Close to 146A; at the margins, close to 146C; venation, close to NN137B. Fully expanded leaves, lower surface: Close to 146B; at the margins, close to 146C; venation, close to 147B.

Inflorescence description:

*Appearance and flowering habit*.—Showy zygomorphic flowers arranged on axillary simple or branched racemes; typically two inflorescences develop per plant; each inflorescence with about 14 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about five months after planting; plants flower naturally during the winter into the spring.

*Flower longevity*.—Long flowering period, individual inflorescences last for about four weeks on the plant; flowers not persistent.

*Inflorescence length* (*lowermost flower to inflorescence apex*).—About 18.5 cm.

*Inflorescence width*.—About 15.5 cm.

*Flower buds*.—Height: About 1.6 cm. Diameter: About 1.2 cm by 1.3 cm. Shape: Broadly ovate. Color: Close to 186C; towards the apex, tinged with close to 148D; venation, close to 186A.

*Flower size*.—About 4.7 cm (vertical) by 6 cm (horizontal).

*Flower depth*.—About 3.7 cm.

*Petals, quantity and arrangement*.—Three, two lateral petals and one center petal transformed into a labellum.

*Lateral petals*.—Length: About 3 cm. Width: About 3.1 cm. Shape: Roughly lunate to broad rhomboidal-reniform. Apex: Obtuse. Margin: Entire; not undulate. Texture and luster, upper and lower surfaces: Smooth, glabrous, velvety; matte. Color: When opening, upper surface: Upper half of petal is close to 76A and 76B and heavily blotched with close to 71A and N79C; lower half of petal is close to a blend of 76D and N155A and slightly to heavily blotched with close to N78A and N79C; towards the margins, close to 76C and at the marginal edges, close to NN155D; at the base, close to N78B and N78C. When opening, lower surface: Close to N75D and 76A; upper half of petal is heavily blotched with close to 72A and 72B; lower half of petal is slightly to heavily blotched with close to 72B and 72C; towards the margins, close to 76C to 76D; at the base, close to N78C. Fully opened, upper surface: Upper half of petal is close to 76B and 76C and heavily blotched with close to N79B and N79C; lower half of petal is close to a blend of 76C and N155A and slightly to heavily blotched with close to N78A and N79C; towards the margins, close to 76B and at the marginal edges, close to NN155D; at the base, close to N78A and N78B; color does not change with subsequent development. Fully opened, lower surface: Close to N75B; upper half of petal is heavily blotched with close to N79C, N79D, N80B and N80C; lower half of petal is slightly to heavily blotched with close to N79C and N79D; towards the margins, close to 76C and at the marginal edges, close to NN155D; at the base, close to N78B; color does not change with subsequent development.

*Labella*.—Appearance: Three-parted with two lateral lobes and a central lobe. Length, lateral lobes: About 1.6 cm. Width, lateral lobes: About 1.2 cm. Length, central lobe: About 1.8 cm. Width, central lobe: About 4 mm to 17 mm. Length, cirrhose tips: About 1 cm. Shape, lateral lobes: Obovate. Shape, central lobe: Deltoid with a slightly elongated apex. Apex, lateral lobes: Obtuse. Apex, central lobe: Cleft with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 5 mm in width and about 4 mm in height. Color: When opening, upper surface: Lateral lobes: Close to NN155D; lower margins, close to 5A; at the base, close to 183B. Central lobe: Close to 4A; towards the apex, close to NN155D; narrow marginal edges, close to 22B; towards the base, close to 59A and 59B and at the base, close to NN155D; cirrhose tips, close to NN155D. Callosities: Close to 176A; towards the base, close to NN155D and occasionally with blotches, close to 12A. When opening, lower surface: Lateral lobes: Close to NN155D; lower margins, close to 4A; at the base, close to 201D tinged with close to 182C. Central lobe: Close to 75C; towards the margins and apex, close to 155B; towards the base, close to 8B and at the base, close to a blend of N187D and 201D; cirrhose tips, close to NN155A. Fully opened, upper surface: Lateral lobes: Close to NN155D; lower margins, close to 12A; at the base, close to 183B. Central lobe: Close to 20B; towards the apex, close to NN155D; towards the base, close to 59A and 59B and at the base, close to NN155D; cirrhose tips, close to NN155D. Callosities: Close to 178A; towards the base, close to N155A and occasionally with blotches, close to 17C. Fully opened, lower surface: Lateral lobes: Close to NN155D; lower margins, close to 13B; at the base, close to 201D tinged with close to 182B. Central lobe: Close to 75C; towards the margins and apex, close to NN155D; towards the base, close to 11A and 11B and at the base, close to a blend of N187D and 201D; narrow marginal edges, close to 22A; cirrhose tips, close to NN155D.

*Sepals*.—Quantity and arrangement: Three, one upper dorsal sepal and two lower lateral sepals. Length, dorsal sepal: About 2.9 cm. Width, dorsal sepal: About 1.9 cm. Length, lateral sepals: About 3.2 cm. Width, lateral sepals: About 2.1 cm. Shape, dorsal sepal: Broadly elliptic. Shape, lateral sepals: Ovate. Apex, dorsal sepal: Retuse. Apex, lateral sepals: Acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 76B; towards the base, close to 76C and 76D; heavily blotched with close to 59A, N79B and N79C. When opening, lower surface: Close to 186D; towards the apex and base, close to 75A; heavily blotched and dotted with close to 71A and N79C; venation, close to N77B. Fully opened, upper surface: Close to 76C; towards the apex, close to N75D; towards the base, close to 76A; heavily blotched with close to N79B and N79C. Fully opened, lower surface: Close to N80C; towards the apex, close to N80B; towards the base, close to N80D; heavily blotched and dotted with close to N79B; venation, close to N77B. Color, lateral sepals: When opening, upper surface: Close to 76D; towards the apex, close to 76C; upper half, slightly to moderately blotched with close to N79C. When opening, lower surface: Close to 75A and 75B; upper half, moderately blotched and dotted with close to N79C. Fully opened, upper surface: Close to 76B and 76C; center, close to 76D; upper half, slightly to moderately blotched and dotted with close to N79B and N79C. Fully opened, lower surface: Close to N78D; towards the apex, close to N78C; upper half, moderately blotched and dotted with close to N79B and N79C; venation, close to N78B.

*Peduncles*.—Length: About 34 cm. Diameter: About 4 mm. Aspect: Upright to outwardly arching. Texture and luster: Smooth, glabrous; matte. Color: Close to a blend of N200A and N200B; heavily dotted with fine dots, close to 146C.

*Pedicels*.—Length: About 2.6 cm. Diameter: About 3 mm. Aspect: About 60° from peduncle axis. Texture and luster: Smooth, glabrous; matte. Color: Close to 145A; proximally, tinged with close to 75D and distally, close to 156D.

Reproductive organs.—Androecium: Column length: About 8 mm. Column width: About 5 mm. Column color: Close to NN155D; towards the apex, blotches, close to N75A. Pollinia quantity: Two. Pollinia diameter (per two pollinia): About 2 mm. Pollinia color: Close to 25B. Gynoecium: Stigma length: About 3 mm. Stigma width: About 3.5 mm. Stigma shape: Reniform. Stigma color: Close to N155A. Ovary length: About 1.3 cm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA964388' as herein illustrated and described.

* * * * *